(12) United States Patent
Testerman et al.

(10) Patent No.: US 7,890,178 B2
(45) Date of Patent: Feb. 15, 2011

(54) METHOD AND APPARATUS FOR ASSISTING DEGLUTITION

(75) Inventors: Roy L. Testerman, New Hope, MN (US); Jon P. Davis, Saint Michael, MN (US); Nathan Andrew Torgerson, Andover, MN (US); Robyn Lee Jagler, Eagan, MN (US); James Britton Hissong, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 355 days.

(21) Appl. No.: 11/611,365

(22) Filed: Dec. 15, 2006

(65) Prior Publication Data

US 2008/0147141 A1 Jun. 19, 2008

(51) Int. Cl.
*A61N 1/08* (2006.01)
(52) U.S. Cl. ........................................................ 607/48
(58) Field of Classification Search .................. 607/48, 607/42
See application file for complete search history.

(56) References Cited

U.S. PATENT DOCUMENTS

| | | | |
|---|---|---|---|
| 4,602,624 A | 7/1986 | Naples et al. |
| 5,193,539 A | 3/1993 | Schulman et al. |
| 5,193,540 A | 3/1993 | Schulman et al. |
| 5,324,316 A | 6/1994 | Schulman et al. |
| 5,344,438 A | 9/1994 | Testerman et al. |
| 5,725,564 A | 3/1998 | Freed et al. |
| 5,843,147 A | 12/1998 | Testerman et al. |
| 5,891,185 A | 4/1999 | Freed et al. |
| 5,987,359 A | 11/1999 | Freed et al. |
| 6,104,958 A | 8/2000 | Freed et al. |
| 6,198,970 B1 | 3/2001 | Freed et al. |
| 6,343,232 B1 | 1/2002 | Mower |
| 6,907,293 B2 | 6/2005 | Grill et al. |
| 6,978,787 B1 * | 12/2005 | Broniatowski ............... 128/898 |
| 7,037,266 B2 | 5/2006 | Ferek-Petric et al. |
| 2002/0049479 A1 | 4/2002 | Pitts |

(Continued)

FOREIGN PATENT DOCUMENTS

WO 2004/028433 A2 4/2004

(Continued)

OTHER PUBLICATIONS

"Lateral Cricoarytenoid muscle" http://en.wikipedia.org/wiki/Lateral_cricoarytenoid_muscle. Jun. 17, 2005.*

(Continued)

*Primary Examiner*—Eric D. Bertram
(74) *Attorney, Agent, or Firm*—Dicke, Billig & Czaja, PLLC (57) ABSTRACT

Artificially stimulated deglutition methods and systems including providing a portable system born by a user for controlling a component of a complete swallowing act without substantial aspiration. The system includes a controller, a signal generator, and a subcutaneously positioned electrode array with at least one electrode. The electrode array is subcutaneously positioned and is operated to stimulate a single deglutition muscle where the single deglutition muscle is the only deglutition muscle directly artificially stimulated via the electrode array during the complete swallowing act. Systems and methods of nerve stimulation and selective nerve stimulation are also provided to artificially stimulate deglutition.

10 Claims, 6 Drawing Sheets

U.S. PATENT DOCUMENTS

| | | | |
|---|---|---|---|
| 2002/0133194 A1 | 9/2002 | Leelamanit et al. | |
| 2003/0093128 A1 | 5/2003 | Freed et al. | |
| 2004/0172092 A1* | 9/2004 | Greenberg et al. | 607/48 |
| 2004/0215236 A1 | 10/2004 | Lattner et al. | |
| 2004/0220645 A1 | 11/2004 | Freed et al. | |
| 2007/0123950 A1* | 5/2007 | Ludlow et al. | 607/42 |
| 2008/0027502 A1* | 1/2008 | Ransom | 607/42 |
| 2008/0103545 A1* | 5/2008 | Bolea et al. | 607/42 |

FOREIGN PATENT DOCUMENTS

| | | |
|---|---|---|
| WO | 2004/028433 A2 | 4/2004 |

OTHER PUBLICATIONS

A PCT Search Report mailed Mar. 14, 2008 (6 pgs.).

A PCT Written Opinion mailed Apr. 18, 2008; 6 pgs.

W.M. Grill, "Inversion of the Current-Distance Relationship by Transient Depolarization," IEEE Transations on Biomedical Engineering, vol. 44, No. 1, Jan. 1997; 9 pgs.

R.W. Doty et al., "An Electromyographic Analysis of Reflex Deglutition," J. Neurophysiol 19: 44-60; 1956.

W.M. Kraus, et al., "Transtracheal/Transesophageal Stimulation of the Recurrent Laryngeal Nerve," Laryngoscope 97: 663; 1987.

M. Friedman et al. "Implantation of a Recurrent Laryngeal Nerve Stimulator for the Treatment of Spastic Dysphonia," Amn. Otol Rhinol Laryngol 98: 130-134; 1989.

D.K. Peterson et al., "Electrical Activation of Respiratory Muscles by Methods Other than Phrenic Nerve Cuff Electrodes," PACE 12: 854-860; 1989.

C.L. Ludlow et al., "Successful Treatment of Selected Cases of Abductor Spasmodic Dysphonia Using Botulinum Toxin Injection," Otolaryngol Head Neck Surg 104: 849-855; 1991.

J. Koda et al., "An Evaluation of Laryngeal Muscle Activation in Patients with Voice Tremor," Otolaryngol Head Neck Surg 107: 684-696; 1992.

M. Broniatowski et al., "Electronic Control of Laryngeal Spasm. II. Selective Blockage of Glottic Adduction by a Closed-Loop Circuit in the Canine," Laryngoscope 103: 734-740; 1993.

D.K. Peterson et al., "Long-Term Intramuscular Electrical Activation of the Phrenic Nerve: Safety and Reliability," IEEE Trans Biomed Eng 41(12): 1115-1126; 1994.

M. Broniatowski et al., "Artificial Reflex Arc: A Potential Solution for Chronic Aspiration. III. Stimulation of Implanted Cervical Skin as a Functional Graft Triggering Glottic Closure in the Canine," Laryngoscope 104: 1259-1263; 1994.

M. Broniatowski et al., "Electronic Integration of Glottic Closure and Cricopharyngeal Relaxation for the Control of Aspiration: A Canine Study," Otolaryngol Head Neck Surg 112: 424-429; 1995.

A.R. Schwartz et al., "Electrical Stimulation of the Lingual Musculature in Obstructive Sleep Apnea," J. Appl Physiol 81(2): 653-652; 1996.

E.A. Nash et al., "Laryngeal Muscle Activity During Speech Breaks in Adductor Spasmodic Dysphonia," Laryngoscope 106: 484-489; 1996.

W.M. Grill et al. "Inversion of the Current-Distance Relationship by Transient Depolarization," IEEE Trans Biomed Eng 44: 1-9; 1997.

G.S. Goding, Jr. et al., "Relief of Upper Airway Obstruction with Hypoglossal Nerve Stimulation in the Canine," Laryngoscope 108: 162-169; 1998.

C.L. Ludlow et al., "Three-Dimensional Changes in the Upper Airway During Neuromuscular Stimulation of Laryngeal Muscles," Artif. Organs 23(5): 463-465; 1999.

W.M. Grill et al., "Emerging Clinical Applications of Electrical Stimulation: Opportunities for Restoration of Function," J. Rehabil Res Dev 38(6): 641-653; 2001.

V. Leelamanit et al., "Synchronized Electrical Stimulation in Treating Pharyngeal Dysphagia," Laryngoscope 112: 2204-2210; 2002.

J.M. Barkmeier et al., "Laryngeal Activity During Upright vs. Supine Swallowing," J. Appl Physiol 93(2): 740-745; 2002.

T.A. Burnett et al., "Laryngeal Elevation Achieved By Neuromuscular Stimulation at Rest," J. Appl Physiol 94(1): 128-134; 2003.

M.D. Tarler et al., "Selective and Independent Activation of Four Motor Fascicles Using a Four Contact Nerve-Cuff Electrode," IEEE Trans Neural Syst Rehabil Eng 12(2): 251-257; 2004.

B.T. Massey et al., "Introduction to the Field of Deglutition and Deglutition Disorders," In: A.L. Periman et al., "Deglutition and its Disorders." Singular Publishing Group, Inc., San Diego; 13 pgs. (1997).

C.L. Ludlow et al., "Effects of Surface Electrical Stimulation Both at Rest and During Swallowing in Chronic Pharyngeal Dysphagia," 10 pgs.; Dysphagia 22:1-10 (2007).

* cited by examiner

METHOD AND APPARATUS FOR ASSISTING DEGLUTITION

BACKGROUND

The present invention relates to systems and methods for assisting deglutition, and more particularly to systems and methods for stimulating deglutition musculature in order to reduce effects of dysphagia.

The condition of having an inability to swallow is generally described as "dysphagia." Dysphagia is commonly associated with ailments such as strokes, neurodegenerative diseases, brain tumors, respiratory disorders, and others. In some forms, dysphagia results in aspiration during "deglutition," the act of swallowing. Aspiration during deglutition is of great concern as it increases the risk of aspiration pneumonia. In particular, there is evidence that aspiration pneumonia inflicts about a 20% death rate in the first year after a stroke and about a 10% to 15% death rate each year thereafter. Traditional treatments for dysphagia have employed either temporary feeding through a nasogastric tube or enteric feeding through a stoma to the stomach in chronic cases.

Techniques of electrical stimulation of electrically excitable tissue within the body of a living subject have been developed utilizing stimulating electrodes and a signal generator to supply electrical charges in a controlled or predetermined manner. PCT App. Pub. WO 2004/028433 ("Ludlow") (entitled "Methods and Devices for Intramuscular Stimulation of Upper Airway and Swallowing Muscle Groups;" published Apr. 8, 2004) describes stimulation of muscles within a neck region of a human subject for the purpose of causing muscles to react as a swallowing effect. More specifically, Ludlow describes inducement of swallowing in a subject's body by implanting electrodes in two or more muscles of the upper airway musculature and connecting the electrodes with a signal generator that provides coordinated control signals. Other techniques and methods of artificial stimulation using transcutaneous, non-implanted systems are disclosed in U.S. Pat. Nos. 5,725,564; 5,891,185; 5,987,359; 6,104,958; and 6,198,970, all to Freed et al.

SUMMARY

Some aspects relate to methods for stimulating multiple deglutition responses in a user, for example. In some embodiments, such methods include providing a portable system born by a user for controlling a component of a complete swallowing act without substantial aspiration. The system includes a controller, a signal generator, and an electrode array including at least one electrode. The electrode array is subcutaneously positioning in stimulating communication with at least one deglutition muscle. A single deglutition muscle is artificially stimulated to cause the component of the complete swallowing act to occur. In particular, the single deglutition muscle is the only deglutition muscle directly artificially stimulated via the electrode array during the complete swallowing act.

Other aspects relate to systems for assisting user deglutition by only stimulating a single deglutition muscle. In some embodiments, the systems include an electrode array adapted to be subcutaneously implanted to stimulate the single deglutition muscle. A signal generator is also included and is adapted to communicate with the electrode array to stimulate the single deglutition muscle. A controller operates the signal generator. In particular, the controller is adapted to operate the signal generator to only directly stimulate the single deglutition muscle with the electrode array.

Yet other aspects relate to methods of controlling deglutition of a user without substantial aspiration, for example. In some embodiments, such methods include subcutaneously positioning a first electrode array at a first location along a first nerve, the electrode array including at least one electrode and the first nerve causing activation of a first deglutition muscle. The first nerve is stimulated with the first electrode array to artificially activate the first deglutition muscle.

Still other aspects relate to systems for assisting user deglutition, for example. In some embodiments, such systems include an electrode array adapted to be subcutaneously implanted to stimulate a first nerve, the first nerve causing activation of a first deglutition muscle. The electrode array includes at least one electrode. The system also includes a signal generator. The signal generator is adapted to communicate with the electrode array to stimulate the first nerve. A controller operates the signal generator. In particular, the controller is adapted to operate the signal generator to stimulate the first nerve with the electrode array to cause activation of the first deglutition muscle.

DETAILED DESCRIPTION

In order to provide a better understanding of various embodiments, the following description has been formatted with several headings. However, it is to be understood that such headings are not intended as limiting, and that description is intended to be read as a whole, as a cumulative narrative of various embodiments with interrelating features where appropriate. With that in mind, descriptions of the following, general topics are provided: Deglutition Assistance Systems Overview; Overview of Deglutition; Artificial Deglutition Muscle Stimulation via Nerves; Muscle Activation Patterns and Associated Stimulation Patterns; Single Muscle Stimulation and Select Muscle Group Stimulation; Stimulation Program Initiation and Selection; and System Feedback.

Deglutition Assistance Systems Overview

Figure 1:
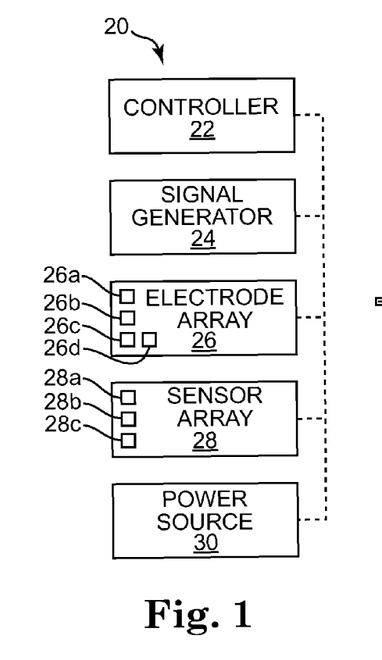
FIG. 1 is a schematic view of a system for assisting deglutition according to some embodiments.

FIG. 1 is a schematic view of a system 20 for assisting deglutition. The system 20 includes a controller 22, a signal generator 24, an electrode array 26 including at least one electrode, a sensor array 28 including at least one sensor, and a power source 30. In some embodiments, various components of the system 20 are maintained in an implantable housing 32 (FIG. 6), which is optionally substantially similar to a pacemaker "can," with an external switch or sensor (FIG. 6) optionally included for activating the system 20. As indicated generally by dotted lines, the various aspects of the system 20 communicate with one another, such communication being accomplished via a variety of mechanisms. For example, the components are optionally in direct, electrical communication; radio frequency communication; magnetic communication; optical communication; sonic communication; combinations thereof, and others.

The system 20 is generally adapted to control deglutition musculature. In some embodiments, the system 20 is portable and adapted to be born by a user, for example a chronic dysphagia sufferer, for extended periods of time. The controller 22, the signal generator 24, the electrode array 26, the sensor array 28, and/or the power source 30, or portions thereof, are provided as separate, distinct components; as partially integrated components; or as fully integrated components as desired. For example, some embodiments include one or more integrated electrodes having processing, signal generating, external communicating, and/or sensing capabilities, one or more of which are fully or partially integrated into the integrated electrode(s).

In some embodiments, the controller 22 includes a microprocessor, a hardwired circuit, or other appropriate means for controlling various aspects of the system 20. In particular, the controller 22 operates the signal generator 24 and/or receives information from various sources, such as the sensor array 28. In some embodiments, the controller 22 is adapted to store a stimulation program or programs and operate the signal generator 24 according to the stimulation program(s). Stimulation programs include predetermined, set programs, for example hardwired into the controller 22, but can also include adaptive, dynamic programs, for example software that adapts artificial deglutition stimulation according to various inputs, such as input from the sensor array 28.

It follows that, in some embodiments, the controller 22 selects between various programs and/or actively modifies a stimulation program according to various inputs, such as information received from a user, information received from the sensor array 28, information received from the signal generator 24, information received from the electrode array 26, information received from a remote processor (not shown), and/or information received from a technician or surgeon, for example.

The signal generator 24 is in communication with the electrode array 26 and is adapted to provide one or more stimulating signals to the electrode array 26. In some embodiments, the simulating signals communicate stimulating energy, such as electrical current pulses, to the electrode array 26 in order to activate deglutition musculature. As described in greater detail below, the signal generator 24 optionally includes circuitry and/or other implantable components for outputting electrical pulses through electrical leads to the electrode array 26. For example, the stimulating signals are optionally a series of overlapping, electrical current pulse trains communicated to the electrode array 26 and ultimately to deglutition musculature. It is also contemplated that the signal generator 24 optionally communicates power to the electrode array 26 via other mechanisms than electrical connection, for example radiofrequency power transmission and/or magnetic power transmission.

Additionally, or alternatively, signals from the signal generator 24 can be otherwise communicative in nature, for example, communicating stimulation program information, patient information, and other types of information. In some embodiments, the signal generator 24 includes a radio frequency transmitter communicating with a self-contained electrode acting as a receiver, i.e., an electrode that is not physically "wired" to a separate signal generator via electrical leads or other means. In particular, the self-contained electrode receives the radio frequency transmission as a source of power and/or as a control signal for timing delivery of stimulating energy to deglutition musculature. It should also be noted that in some embodiments, the self-contained electrodes include an associated signal generator for providing stimulating signals to the particular self-contained electrode. For reference, embodiments of self-contained electrodes and various examples of stimulation signal patterns and stimulation programs are subsequently described in association with methods of artificially stimulating deglutition.

As previously alluded to, unless specified otherwise, the controller 22 and the signal generator 24 (as well as other components of the system 20) are configured as separate, distinct components; partially integrated components; or fully integrated components as desired. As one example, a combined controller 22 and signal generator 24 include a shared processor or processors providing a stimulating signal to the electrode array 26 in the form of an electrical current output or other appropriate output from the processor. Thus, in the absence of limiting language, such as "wherein the signal generator 24 and the controller 22 are separate, distinct components," "the signal generator 24 being apart from the controller 22," or alternatively "wherein the signal generator 24 and the controller 22 are fully integrated," for example, it is contemplated that the controller 22 and signal generator 24 are not so limited.

The electrode array 26 includes one or more electrodes, such as a first electrode 26a, a second electrode 26b, and a third electrode 26c. The electrode array 26 is adapted be in stimulating communication with deglutition musculature, for example via subcutaneous, intramuscular placement; subcutaneous, exterior placement on a muscle surface; and/or subcutaneous implantation and association with one or more nerves controlling deglutition musculature. Alternatively, one or more electrodes of the electrode array 26 are adapted for percutaneous application or application external to skin, for example.

In some embodiments, the electrode array 26 includes one or more of the following types and/or categories of electrodes: epimysial electrodes; intramuscular electrodes, such as Peterson electrodes; nerve cuff electrodes; self-contained electrodes; monopolar electrodes; bipolar electrodes; multi-contact electrodes; and/or other known electrode types/categories and combinations thereof. As described in greater detail below, in some embodiments, the electrode array 26 includes one or more associated flexible, extensible electrical leads suited for use in deglutition stimulation applications, such as those described in co-pending U.S. application Ser. No. 11/413,316 (entitled "Implantable Medical Leads And Lead Assemblies With Improved Flexibility And Extensibility To Facilitate Body Movements"); Ser. No. 11/413,435 (entitled "Methods For Customizing Implantable Medical Lead Assemblies With Improved Flexibility And Extensibility"); Ser. No. 11/413,437 (entitled "Implantable Medical Assemblies With Improved Flexibility, Extensibility, And Positionability With Branched Structures"); and Ser. No. 11/413,440 (entitled "Implantable Medical Leads And Lead Assemblies With Improved Flexibility And Extensibility And Having A Substantially Two-Dimensional Nature"); all filed on Apr. 28, 2006 and the contents of each of which are incorporated herein by reference (cumulatively referred to herein as "the Extensible Lead Applications").

Figure 2:
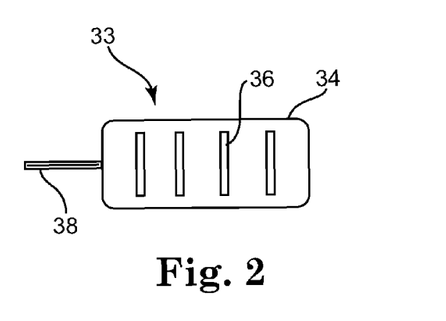
FIG. 2 shows an epimysial electrode according to some embodiments.
Figure 3:
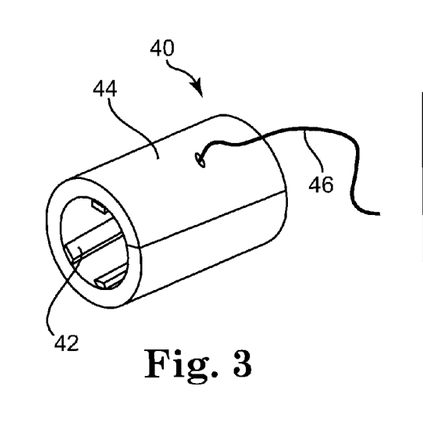
FIG. 3 shows a nerve cuff electrode according to some embodiments.

For general reference purposes, FIG. 3 shows an epimysial electrode 33 useful as, or as part of, the electrode array 26

(FIG. 1) in accordance with some embodiments. The epimysial electrode 33 includes an insulated housing 34 and one or more contacts 36 maintained by the insulated housing 34. An electrical lead 38 is connected to the epimysial electrode 33 to provide an electrical conduit to each contact 36 on an individual or ganged basis as desired. In some embodiments, the epimysial electrode 33 includes a single contact 36 and is monopolar to reduce overall size and/or provide increased overall structural flexibility.

The epimysial electrode 33 is adapted to be secured to a muscle surface, for example by sewing or other appropriate means. In some embodiments, the epimysial electrode 33 helps avoid problems associated with intramuscular electrodes, such as plunging intramuscular electrodes into tissue located behind a target muscle. For example, the epimysial electrode 33 can exhibit less tissue reaction than intramuscular electrodes and is well-suited for use with what can be considered relatively thin deglutition muscles according to some embodiments. Examples of epimysial electrodes can be found in U.S. Pat. No. 5,843,147, issued Dec. 1, 1998, to Testerman et al. and entitled "Implantable Eyelid Electrode and Method of Implanting the Same," the contents of which are incorporated herein by reference.

FIG. 3 is a simplified view of a nerve cuff electrode 40 useful as, or as part of, the electrode array 26 (FIG. 1). The nerve cuff electrode 40 includes a plurality of radially disposed contacts 42 maintained by a tubular, insulated housing 44. The nerve cuff electrode 40 is connected to an electrical lead 46 providing an electrical conduit to each of the plurality of contacts 42, for activation either individually or on a ganged basis as appropriate. In general terms, the nerve cuff electrode 40 is adapted to be disposed about, and in stimulating communication with nerves to deliver stimulating energy to the nerves. In some embodiments, the nerve cuff electrode 40 is substantially U-shaped, for example as described in U.S. Pat. No. 5,344,438, issued Sep. 6, 1994 to Testerman et al., and entitled "Cuff Electrode," the contents of which are incorporated herein by reference. Other examples of suitable nerve cuff electrodes include the self-sizing electrode cuffs described in U.S. Pat. No. 4,603,624, issued Jul. 29, 1986 to Naples et al. and entitled "Cuff, Method of Manufacture, and Method of Installation." As described in greater detail below, the nerve cuff electrode 40 is adapted to selectively stimulate muscles controlled by nerves in some embodiments. For example, the nerve cuff electrode 40 is optionally adapted to allow individual energizing of the radially disposed contacts 42 using a multi-channel signal generator, such as the signal generator 24 (FIG. 1), in order to effectuate current steering techniques, or is otherwise adapted to selectively stimulate nerve fascicles of a nerve as desired.

Returning to FIG. 1, as used herein, "self-contained electrodes" refer to electrodes that are not "hardwired" to the signal generator 24 and/or include their own signal generator, such as those described in the Schulman patents subsequently referenced herein. For example, the signal generator 24 optionally communicates and/or supplies power to the electrode array 26 via radiofrequency transmission and/or magnetic transmission mechanisms. Still further, in some embodiments, self-contained electrodes, or alternately "hardwired" electrodes if desired, are optionally integrated with various control/operation components, such as a signal generator and/or processor for controlling electrode activation, a power source for providing power to activate the electrode, and one or more contacts for receiving/conveying stimulating energy.

Figure 4:
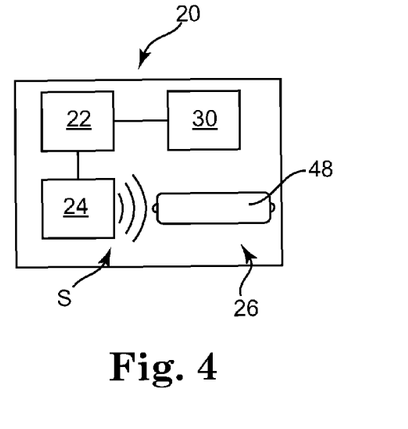
FIG. 4 is a schematic view of the system of FIG. 1 including a self-contained electrode according to some embodiments.

FIG. 4 is a schematic view of an embodiment where the system 20 includes at least one self-contained electrode 48 useful as, or as a part of, the electrode array 26. The self-contained electrode 48 is shown receiving a signal S, for example a radiofrequency and/or magnetic signal, from a transmitter (not shown) provided with the system 20. In some embodiments, the self-contained electrode 48 is an implantable microstimulator, such as those described in U.S. Pat. No. 5,193,539, issued Mar. 16, 1993, to Schulman et al. and entitled "Implantable Microstimulator;" U.S. Pat. No. 5,193,540, issued Mar. 16, 1993, to Schulman et al. and entitled "Structure and Method of Manufacture of an Implantable Microstimulator;" and U.S. Pat. No. 5,324,316, issued Jun. 28, 1994, to Schulman et al. and entitled "Implantable Microstimulator" (collectively referred to herein as "the Schulman patents"), the contents of all of which are incorporated herein by reference. For example, the controller 22 and/or the signal generator 24 optionally include an electrical coil (not shown) and are provided externally to a dysphagia sufferer, with the self-contained electrode 48 being subcutaneously implanted. In some embodiments, the system 20 is configured such that the self-contained electrode 48 receives power and/or stimulation commands through the signal S, for example with the signal S being an AC magnetic link established between the signal generator 24 and the self-contained electrode 48 using the external electrical coil.

Returning to FIG. 1, the sensor array 28 includes one or more sensors, such as a first sensor 28a, a second sensor 28b, and a third sensor 28c. The sensor array 28 is adapted to provide information relating to deglutition and/or the system 20. The sensor array 28 includes sensors adapted for subcutaneous use; exterior placement, for example on skin or hair; and/or percutaneous placement as appropriate. In some embodiments, the sensor array 28 includes one or more force, movement, pressure, and/or position sensors, such as accelerometers; force gauges, for example strain gauges; EMG sensors; displacement sensors, for example sensors using piezo crystals to provide ultrasonic generating/sensing transducers; pressure sensors; and others.

Operating requirements of the various sensors, for example the sensors 28a-28c, are better understood with reference to various embodiment methods of artificially stimulating deglutition using the system 20 that follow. Examples of suitable sensors and/or sensors which are suitably adapted for use with the system 20 can be found, for example, in U.S. Pat. No. 7,037,266, issued May 2, 2006 to Ferek-Petric et al. and entitled "Ultrasound Methods and Implantable Medical Devices Using Same," the contents of which are incorporated herein by reference.

As previously referenced, the power source 30 is a single component or multiple components, and is provided separately and distinct from other components of the system 20 or as an integrated part of other components of the system 20. The power source 30 is optionally a chemical battery, a capacitor, or other appropriate means for powering the system 20. In some embodiments, the power source 30 is adapted to be safely implanted into a living creature, for example a person suffering from dysphagia.

Overview of Deglutition

Figure 5A:
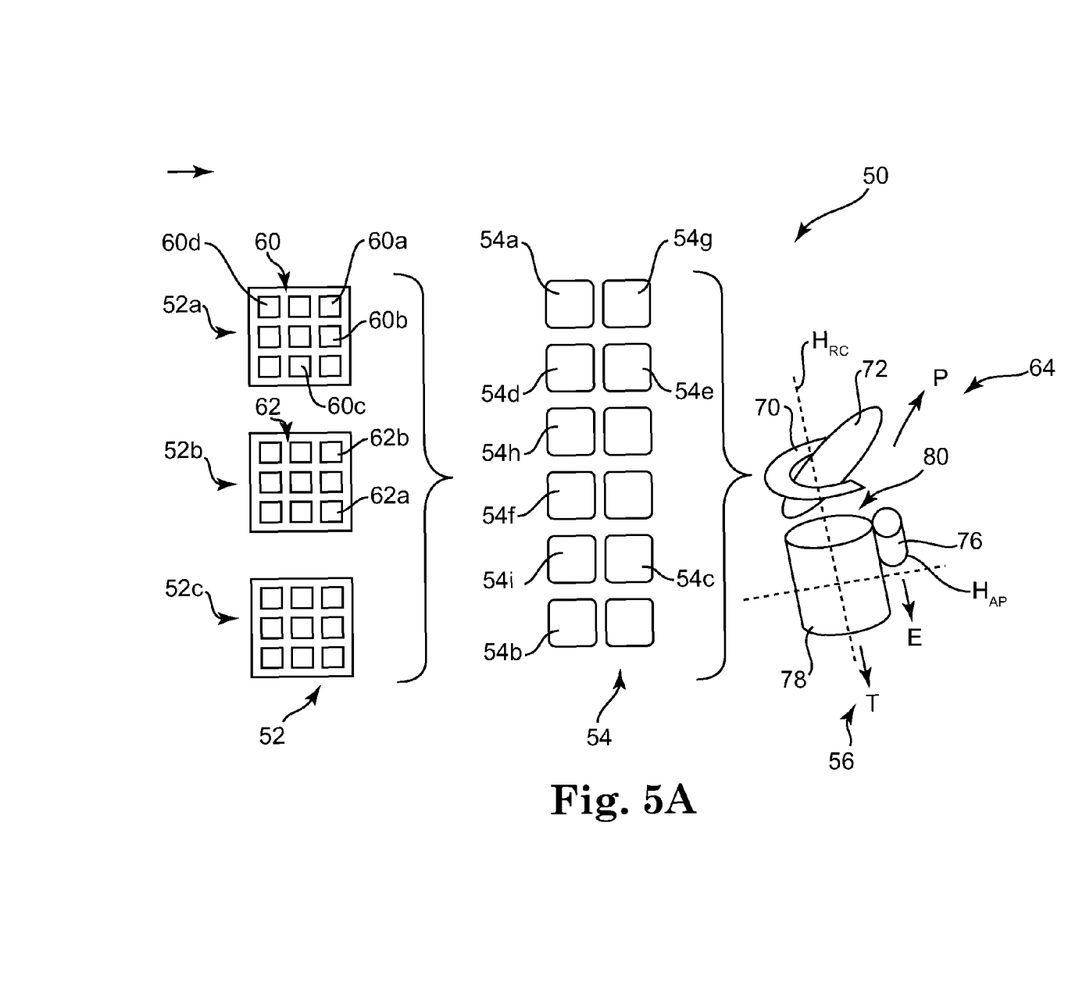
FIG. 5A is a schematic view of bodily components associated with deglutition.
Figure 5B:
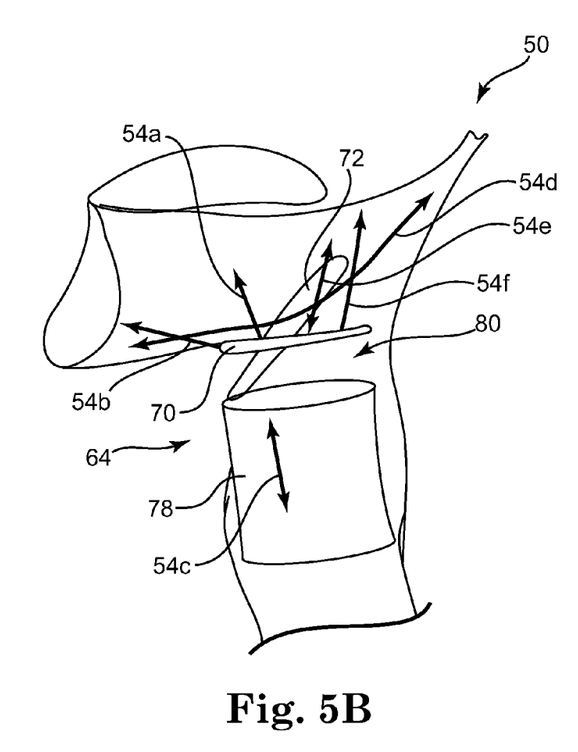
FIG. 5B is a schematic view of a hylayrngeal complex and associated bodily components associated with deglutition.

With the understanding provided by the foregoing, it is useful to give some background on various aspects of deglutition, the act of swallowing, as well as various body parts associated with deglutition prior to describing additional specifics of the system 20 and methods of use thereof. FIG. 5A is a generalized, schematic view of bodily components 50 associated with deglutition. In turn, FIG. 5B is a second, generalized schematic view of some of the bodily components 50 of FIG. 5A presented for additional understanding. Generally speaking, the bodily components 50 are described with reference to human anatomy. However, it is contemplated that, though human anatomy may not be identical to that of other organisms, similar concepts to those described herein are applicable to other living organisms, such as monkeys, cats, dogs, horses, reptiles, or other animals, for example. Regardless, in general terms the bodily components 50 generally include one or more nerves 52, one or more deglutition muscles 54, and one or more deglutition structures 56. As described in greater detail, the nerves 52 perform motor functionality by directly stimulating the deglutition muscles 54 and/or providing sensory activation of the deglutition muscles 54, including via sensory mucosa or muscular sensory endings. In turn, the deglutition muscles 54 move the deglutition structures 56 to complete deglutition, or otherwise effectuate a complete swallowing act.

By way of background, a complete act of swallowing can be broken down into several, basic stages—an oral stage, a pharyngeal stage, and an esophageal stage. Each stage includes a series of movements for effectuating deglutition of a bolus. As used herein, "bolus" refers to any substance to be swallowed, including liquids and solids, unless indicated otherwise. In cases of dysphagia, there is insufficient muscle activity (e.g., timing, type, or amount of activity) during one or more stages of deglutition, such that deglutition is defective. Often times, defective deglutition results in aspiration of the bolus or a portion thereof. At times, a particular case of dysphagia affects swallowing in different manners and/or to different extents according to the individual, including the particular swallowing structures/muscles affected, and/or according to a type/size/consistency of the bolus being swallowed.

Generally, the oral stage entails voluntary control of oral structures, for example controlling the anterior position of the soft palate. During the oral stage, the bolus is typically pushed back in the oral cavity with the tongue. An end portion of the oral stage is generally indicated by the bolus passing the anterior faucial arches of a throat. Typically, the pharyngeal phase commences as an involuntary reflex initiated by the end portion of the oral stage. It should be noted that portions of the three stages often overlap. In some cases of dysphagia, insufficient movement during the oral stage results in a delay of initiation of a beginning portion of the pharyngeal phase, which, in turn, can lead to aspiration during swallowing.

The beginning portion of the pharyngeal stage typically includes using muscles of the hyolaryngeal complex that control hyoid movement and laryngeal elevation to raise or lift the hyolaryngeal complex and move it forward in an anterior direction. Normally, as a part of the pharyngeal stage, thyroarytenoid and ventricular cords are closed to form a velopharyngeal seal. The epiglottis is tilted and an upper esophageal sphincter (UES) is relaxed, opening the esophagus. The UES is located in a cricopharyngeal region and includes a cricopharyngeus muscle which is attached to cricoid cartilage. In some cases of dysphagia there is insufficient lifting/forward movement of the hyolaryngeal complex, insufficient tilting of the epiglottis, and/or insufficient relaxation/opening of the UES, all of which can contribute to aspiration and/or other defects in a complete swallowing act.

A beginning portion of the esophageal stage is typically initiated as the upper esophageal sphincter (UES) opens. The bolus is transferred down the esophagus by a series of peristaltic wave contractions which are typically initiated during the pharyngeal stage. The bolus eventually works its way to the inferior esophageal sphincter and enters the stomach. In some cases of dysphagia, the cricopharyngeal opening remains lax following the pharyngeal stage, and does not sufficiently constrict. This can also result in some material remaining in the pharynx, raising the risk of subsequently aspirating the remaining material.

With the above overview in mind, the bodily components 50 and relative interactions between the bodily components 50 are described in greater detail, beginning with the nerves 52. The nerves 52 include a plurality of nerves, such as a first nerve 52a, a second nerve 52b, and a third nerve 52c. In general terms, the nerves 52 stimulate activation of the deglutition muscles 54 and/or provide sensory feed back relating to deglutition, with each of the nerves 52a, 52b, 52c being formed of a plurality of nerve fibers, such nerve fibers being grouped into nerve fascicles. For example, the first nerve 52a includes a first plurality of nerve fascicles 60, such as a first nerve fascicle 60a, a second nerve fascicle 60b, a third fascicle 60c, and a fourth fascicle 60d. The second nerve 52b also includes a second plurality of nerve fascicles 62, such as a fifth nerve fascicle 62a and a sixth nerve fascicle 62b. As described in greater detail below, when associated with muscular motor response, the nerve fascicles are "tied" to one or more of the deglutition muscles 54, such that a particular nerve fascicle or group of nerve fascicles stimulates or otherwise causes activation of a particular muscle or group of muscles. Some embodiments include selectively stimulating one or more nerve fascicles of a particular nerve to selectively stimulate deglutition muscles associated with the particular nerve.

The first nerve 52a is a hypoglossal nerve with the nerve fascicles 60 activating the geniohyoid, hyoglossus, thyrohyoid, omohyoid, sternothyroid, sternohyoid, genioglossus, and/or styloglossus muscles, for example. In turn, the second nerve 52b is a mylohyoid nerve (from an inferior alveolar nerve) activating the mylohyoid muscle and/or a digastric muscle, for example. The third nerve 52c is a cervicalis nerve activating one or more associated deglutition muscles 54. Although specific examples for the first, second, and third nerves 52a-52c have been provided, it should be understood that the nerves 52 are any of the nerves (including nerve branches, nerve roots, nerve rootlets, etc.) that stimulate musculature associated with deglutition (motor function) and/or carry sensory signals (sensory function). For example, the nerves 52 are selected from one or more of a vagus, hypoglossal, mylohyoid, glossopharyngeus, laryngeal, superior laryngeal, recurrent laryngeal, facial, C1 trigeminal, mandibular, inferior alveolar, and cervical nerves, including the ansa cervicalis, and other nerves.

Figure 8:
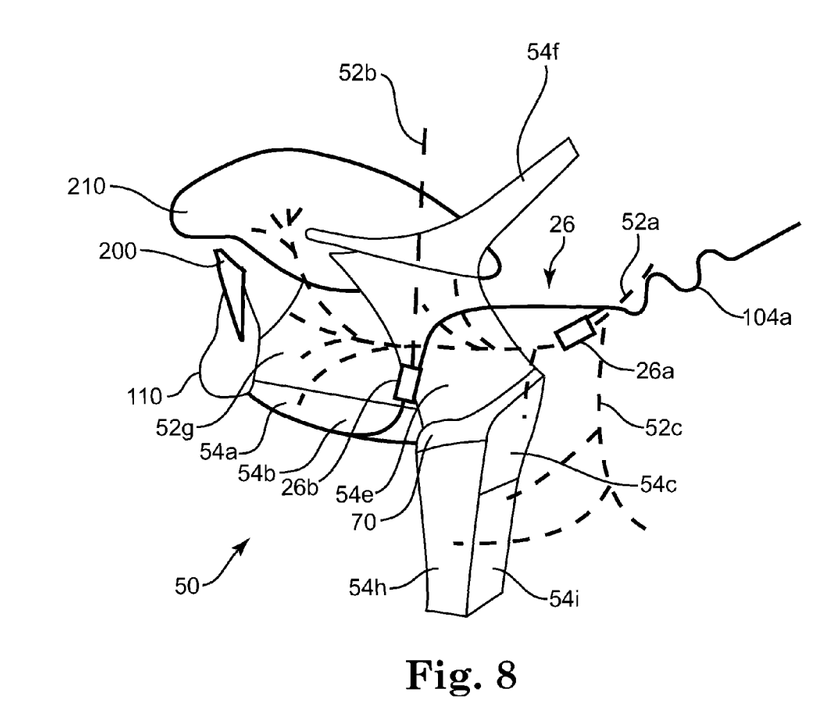
FIG. 8 shows an electrode array of the system of FIG. 1 in stimulating communication with deglutition musculature via a plurality of nerves according to some embodiments.

With reference between FIG. 5A, FIG. 5B, and FIG. 8, and as previously referenced, the deglutition muscles 54 cause movements corresponding to various stages of deglutition. For reference FIG. 5B represents several of the deglutition muscles 54 according to associated directions they move the hyolaryngeal complex 64. The deglutition muscles 54 are generally any of the plurality of muscles causing movements associated with components of deglutition, including muscles associated with any one or more of the oral, pharyngeal, and esophageal stages of deglutition. For illustrative purposes, a first muscle 54a, a second muscle 54b, a third muscle 54c, a fourth muscle 54d, a fifth muscle 54e, a sixth muscle 54f, a seventh muscle 54g an eighth muscle 54h, and a ninth muscle 54i are described. In particular, the muscles 54a-54i are mylohyoid, geniohyoid, thyrohyoid, anterior belly of a digastric, hyoglossus, stylohyoid, genioglossus, sternohyoid, and sternothyroid, respectively.

Though specific ones of the deglutition muscles 54 are listed above, it should be understood that the deglutition muscles 54 also include any one or more of the muscles or muscle groupings selected from the following, non-exclusive list: muscles supporting the larynx and hyoid bone; intrinsic laryngeal muscles, extrinsic laryngeal muscles, posterior intrinsic muscles of the tongue, hyoglossus, genioglossus, thyrohyoid, constrictor pharyngis superior, constrictor pharyngis medius, constrictor pharyngis inferior, cricopharyngeus (UES), digastricus, cricoarytenoid lateralis, geniohyoid, levator veli palatini, mylohyoid, omohyoid, palatoglossus, palatopharyngeus, sternohyoid, sternothyroid, styloglossus, stylohyoid, stylopharyngeus, tensor veli palatine, thyroarytenoid inferior, thyroarytenoid superior, and others. For reference, where a bilateral pair of muscles is implicated, the term "a single deglutition muscle," for example, is indicative of a unilateral one of such a bilateral muscle pair.

The deglutition structures 56 are formed of bone, cartilaginous matter, tissue, muscles (including one or more of the deglutition muscles 54), and/or other materials. In general terms, the deglutition structures 56 include the UES, the epiglottis, the hyoid, and other components of the larynx and/or the pharynx, for example, as well as other deglutition structures.

With reference to the schematic view of FIG. 5A, the deglutition structures 56 include a hyolaryngeal complex 64, components of which are also presented in FIG. 5B. As used herein, the term "hyolaryngeal complex" refers to a deglutition structure of the neck including the larynx, the hyoid, and associated deglutition muscles. With reference to FIG. 5A, the hyolaryngeal complex 64 includes a hyoid 70, an epiglottis 72, a UES 76, and lower laryngeal cartilages 78 defining a vestibule 80. The hyolaryngeal complex 64 defines a rostro-caudal axis $H_{RC}$ and an anterior-posterior axis $H_{AP}$. For reference, and in general terms, the pharynx P (designated generally in the indicated direction) extends to the hyolaryngeal complex 64, where respiratory and digestive pathways diverge. This divergence is characterized by the pharynx P communicating with an esophagus E (designated generally in the indicated direction) posteriorly, where the UES 76 closes off the esophagus E from the pharynx P during breathing. Typically, the esophagus E conducts food and fluids to the stomach as previously described. In turn, air entering from the pharynx P proceeds anteriorly through the laryngeal vestibule 80 to a trachea T (designated generally in the indicated direction) during breathing.

With reference between FIG. 5A and FIG. 5B, during swallowing, the laryngeal vestibule 80 is closed off while material is transported posteriorly into the esophagus E. In particular, during a normal swallow, the hyolaryngeal complex 64 is lifted forward and upward. The epiglottis 72 folds down to close off the laryngeal vestibule 80. This movement helps trigger relaxation of the UES 76 such that food or liquid can pass into the esophagus E.

In a properly functioning swallow, the various movements are involuntarily coordinated to avoid substantial aspiration of a bolus of liquid or solid matter. However, in cases of dysphagia, such deglutition movement is improperly timed and/or insufficient. For example, the hyolaryngeal complex 64 moves an insufficient amount upward and forward, the epiglottis 72 does not fold down sufficiently, and/or the UES 76 does not sufficiently relax in some cases of dysphagia, such that aspiration during deglutition results. As described below, the system 20 (FIG. 1) is usable to assist deglutition and, in particular, reduce or substantially eliminate aspiration during swallowing in dysphagia sufferers.

In view of the above overview of deglutition and dysphagia, various embodiments of the following are described: implantation of the system 20; various stimulation programs carried out by the system 20 and their features; stimulation of a single deglutition muscle and select muscle groups to artificially stimulate deglutition with the system 20; muscle activation patterns and corresponding stimulation patterns for stimulating deglutition muscles; provision of user feedback in order to facilitate timing of user initiated deglutition movement, for example; stimulation of deglutition musculature with the system 20 via associated nerves; and system feedback for controlling artificial deglutition stimulation with the system 20, for example by modifying a stimulation program or programs.

Implantation of Deglutition Assistance Systems

With reference between FIG. 1, FIG. 5A, FIG. 5B, and FIG. 6, various embodiment methods of implanting the system 20 are described. For additional reference, various ancillary procedures, for example, suturing incisions, irrigating surgical sites, applying prophylactic antibiotics, or checking bodily homeostasis, are clearly contemplated, but left from further discussion. In terms of use and configuration, the system 20 is optionally adapted to be portable and subcutaneously implanted and/or otherwise born by a user 90 of the system 20 for sustained periods of time in some embodiments.

Figure 6:
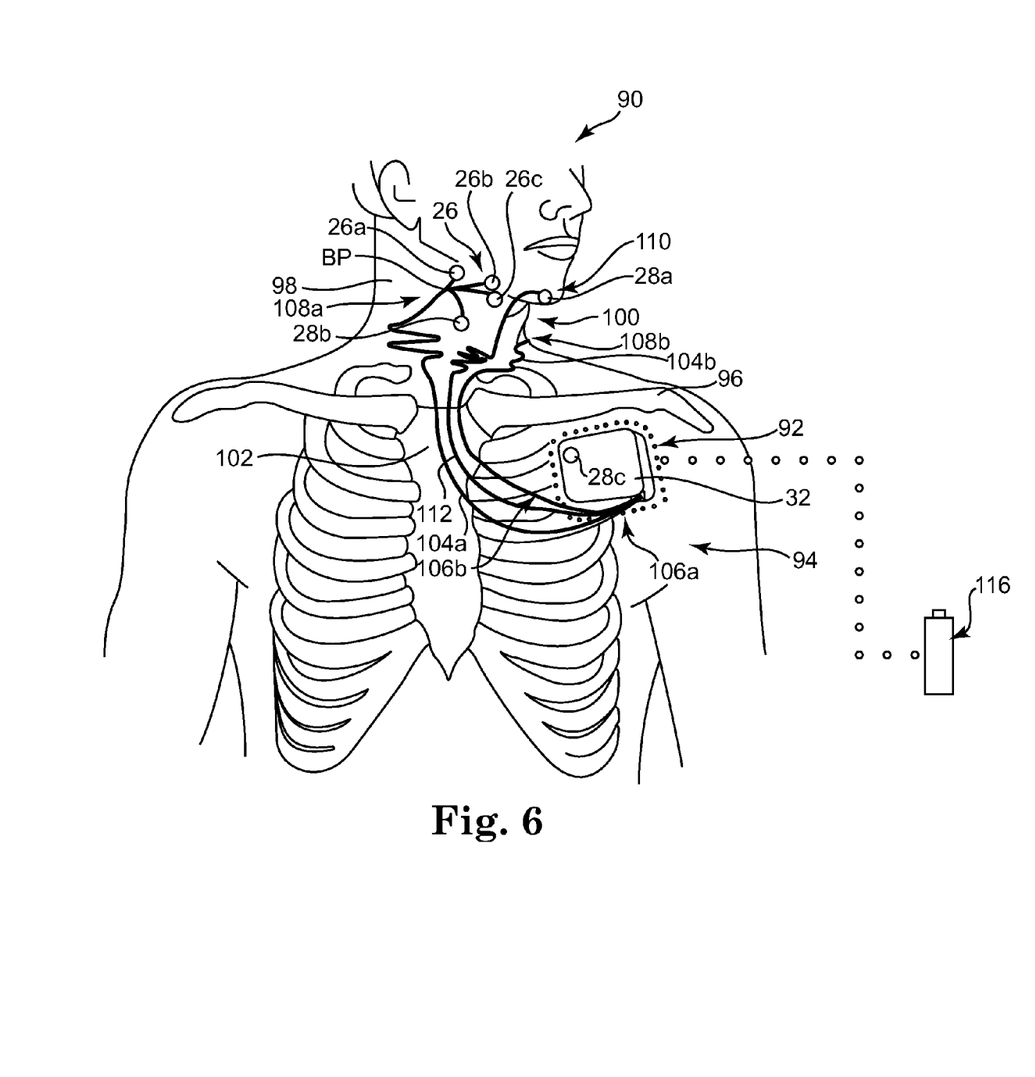
FIG. 6 is a schematic view of an implantable system for assisting deglutition according to some embodiments.

With that in mind, and with particular reference to FIG. 6, implantation of the system 20 generally includes disposing the controller 22, the signal generator 24, and the power source 30 in the implantable housing 32 as a single unit. One or more external devices, such as a hand switch 116, are optionally connected to the controller 22 or are otherwise in communication therewith for user-controlled deglutition stimulation, as will be described in greater detail below. A first incision is made to define a subcutaneous pocket 92 in the upper chest 94 and beneath the clavicle 96 of the user 90 of the system 20. The subcutaneous pocket 92 is sized, shaped, and otherwise formed to maintain the implantable housing 32. The implantable housing 32 is then disposed in the subcutaneous pocket 92. Alternatively, in some embodiments, the controller 22, signal generator 24, and/or power source 30 are optionally left external to the user 90, for example where the electrode array 26 includes self-contained electrodes, for example similar to embodiments of the self-contained electrode 48 previously described.

A second incision, for example a modified apron incision with standard superior and inferior subplatysmal flaps, is formed in a neck 98 of the user 90 at about a thyrohyoid-membrane level 100 of the neck 98. The first and second incisions are connected by forming a first tunnel between the two incisions. The tunnel generally courses under the skin between the first and second incisions over the manubrium 102 of the user 90.

In some embodiments, the electrode array 26 includes a first electrical lead 104a and a second electrical lead 104b, each lead 104a, 104b adapted to form an electrical connection between the electrode array 26 and the signal generator 24. For example, where bilateral muscle stimulation is desired, the second electrical lead 104b is optionally subcutaneously disposed on an opposite side of the neck 98 to the first electrical lead 104a, with corresponding electrodes of the electrode array 26 also subcutaneously positioned in an opposing manner in the neck 98. As referenced above, the electrical leads 104a, 104b are optionally substantially similar to those provided for in the Extensible Lead Applications.

Regardless, the electrical leads 104a, 104b each define first end regions 106a, 106b and second end regions 108a, 108b, respectively. The first end region 106a of the first electrical lead 104a is fed through the first tunnel to the subcutaneous pocket 92. In some embodiments, a third incision substantially similar to the second incision is formed on an opposite side of the neck. A second tunnel is optionally subcutaneously formed from the third incision to the first tunnel, or directly from the third incision to the subcutaneous pocket 92 formed via the first incision, though a variety of manners of subcutaneously positioning the electrical leads 104a, 104b are contemplated. Regardless, the first end region 106b of the second electrical lead 104b is optionally fed through the second tunnel to the subcutaneous pocket 92.

In some embodiments, the electrical leads 104a, 104b each branch out proximate the second end regions 108a, 108b (branching of the second electrical lead 108b is hidden in the view of FIG. 6), such as branching point BP of the first electrical lead 104a. One or more of the points where each of the second end regions 108a, 108b branch out are optionally placed anterior to the sternocleidomastoid muscles of the user 90, although other positions are also contemplated.

Although, as referenced above, FIG. 6 is indicative of bilateral implantation of the electrode array 26 in the neck 98 of the user 90, unilateral implantation is also contemplated, for example using only the first electrical lead 104a. In general terms, bilateral implantation is used to facilitate stimulation of bilateral deglutition musculature although other scenarios are contemplated for bilateral implantation. One or more of the deglutition muscles 54 are identified, such as the thyrohyoid, the hyoglossus, the mylohyoid, and the geniohyoid, and/or any other deglutition muscles 54. Additionally, or alternatively, one or more of the nerves 52 controlling the deglutition muscles 54 (motor function) and/or nerves 54 providing sensory functionality are identified. For example, in some embodiments, visual confirmation and/or neuro-stimulation is used to identify the deglutition muscle(s) 54 and/or nerve(s) 52 of interest.

Following identification of the nerve(s) 52 and/or deglutition muscle(s) 54, one or more electrodes of the electrode array 26, for example the electrodes 26a-26c, are placed in stimulating communication with the selected deglutition muscle(s) 54, either directly or via the nerve(s) 52 related to or otherwise controlling the selected muscle(s) 54. The electrode array 26 is optionally secured in place using a suture, surgical clamp, or other means as appropriate. In some embodiments, placing the electrode array 26 in stimulating communication with deglutition muscle(s) 54 includes: fixing one or more electrodes of the electrode array 26 to a surface of a one or more of the deglutition muscles 54; inserting one or more electrodes into one or more deglutition muscles 54; and/or placing one or more electrodes in stimulating communication with one or more of the nerves 52 causing activation of one or more of the selected deglutition muscle(s) 54.

At some point, the second ends 108a, 108b of the electrical leads 104a, 104b are secured to the implantable housing 32 and placed in communication with the signal generator 24. In turn, the first ends 106a, 106b of the electrical leads 104a, 104b are connected to electrodes of the electrode array 26. It should be noted that in some embodiments, electrodes of the electrode array 26 can also serve sensing functionality, for example serving as a sensor in the sensor array 28. Also of note, the sensor array 28 is optionally implanted with substantially similar techniques to those used in association with the electrode array 26. To provide additional understanding, some embodiment methods of implanting the sensor array 28 are described below in association with the sensors 28a-28c.

In particular, a fourth incision is optionally made at a chin bone, and more specifically the mental protuberance 110 of the mandible of the user 90. The first sensor 28a is subcutaneously affixed to the mental protuberance 110, for example with an adhesive, suture, bone anchor, or other means. The first sensor 28a is optionally connected to one of the first and second electrical leads 104a, 104b. In other embodiments, the first sensor 28a is connected to a third electrical lead 112, such as a flexible, extensible electrical lead, coursing over the manubrium 102 in a substantially similar manner to the first and second electrical leads 104a, 104b.

With reference between FIG. 5A, FIG. 5B, and FIG. 6, the second sensor 28b is optionally inserted through the second or third incision for example, or a fifth incision is optionally made in the neck 98 of the user 90 with the sensor 28b subcutaneously positioned through the fifth incision. The second sensor 28b is optionally secured to a deglutition structure 56, such as the hyolaryngeal complex 64, for example. In some embodiments, the second sensor 28b is secured relative to the hyoid bone 70, the epiglottis 72, or any laryngeal cartilages, including a thyroid cartilage, a cricoid cartilage, an arytenoid cartilage, a cuneiform cartilage, and/or a corniculate cartilage, for example. Additionally, or alternatively, the second sensor 28b is optionally secured relative to the UES 76.

In some embodiments, the second sensor 28b is oriented substantially parallel to the rostro-caudal axis $H_{RC}$ and anterior-posterior axis $H_{AP}$ of the hyolaryngeal complex 64 or a particular component thereof. Where applicable, the second sensor 28b is connected to an electrical lead, for example the second sensor 28b is optionally connected to first electrical lead 104a. From this, it should be understood that the electrical leads 104a, 104b optionally serve multiple purposes, including, for example, conveying stimulating energy to the electrode array 26 along with conveying power to and/or conveying sensor information from the sensor array 28.

With particular reference to FIG. 6, in some embodiments, the third sensor 28c is secured relative to the implantable housing 32 of the system 20. For example the third sensor 28c is optionally implanted prior to, concurrently with, or following, implantation of the housing 32. In some embodiments the third sensor 28c is secured on the implantable housing 32 or otherwise secured such that the third sensor 28c is at a substantially set distance from the implantable housing 32 and in communication with the controller 22 and/or the signal generator 24.

Following implantation of the system 20, various testing and/or optimization of the system 20 is performed as desired. In some embodiments, the system 20 performs a self-configuration operation by stimulating user deglutition using the electrode array 26 and receiving information from the sensor array 28 to optimize deglutition stimulation as described in greater detail below. Following evaluation of the sensor array information, the system 20 modifies a system configuration, for example by changing a stimulation program, to better control user deglutition. In other embodiments, the system 20 is manually configured by a technician or other appropriate personnel. Implantation information regarding implantation of the system 20 is also optionally recorded. For example information relating to electrode type/placement, sensor type/placement, system testing results, and/or other pertinent information is optionally stored remotely or directly in memory associated with the system 20.

Stimulation Program Initiation and Selection

With reference to FIG. 1, following implantation, the system 20 is used to stimulate a component of user deglutition, according to one or more stimulation programs. In particular, the system 20 is adapted for stimulating multiple deglutition responses in the user 90 (FIG. 6) in order to assist one or more components of user deglutition without substantial aspiration. As referenced above, the system 20 optionally stimulates one or more components of user deglutition as part of a method of configuring the system 20, as part of a therapeutic method for teaching the user 90 how to swallow, and/or as part of a method of sustained assistance over an extended period of time, for example.

The system 20 generally activates one or more of the deglutition muscles 54 according to one or more stimulation programs. For example, the controller 22 optionally stores one or more stimulation programs and operates the signal generator 24 according to the desired deglutition program to send stimulating energy to the electrode array 26 for activating the one or more deglutition muscles 54. In some embodiments, the stimulation programs include an active feeding program for stimulating deglutition of at least one of food and drink without substantial aspiration and a passive user secretion maintenance program for stimulating deglutition of user secretions without substantial aspiration. The active feeding program is optionally further divided into specific bolus deglutition program categories according to a bolus characteristic, for example a specialized liquid deglutition program and a specialized solid deglutition program, specialized deglutition programs optimized according to bolus volume or consistency, as well as others, as desired.

Initiation of the active feeding program is optionally under "user control." In particular, the active feeding program, including any specialized deglutition programs, is optionally initiated in response to a user feeding request, for example via an external hand-held switch sensor, such as a hand switch 116 as shown generally in FIG. 6, or via voice command, motion sensor, or one or more of the sensors of the sensor array 28, either "wired" or otherwise in communication with system 20 as described above, for example via radio frequency communication. Thus, in some embodiments, the user is able to provide the system 20 with feeding request information in order to initiate the active feed program.

In some embodiments, the user 90 is able to initiate the active feeding program and sustain deglutition muscle stimulation with the system 20 for a desired period or duration, for example by holding down the hand switch 116 for the desired duration of stimulation. Additionally, stimulation intensity is optionally the subject of user control, for example according to a degree of depression of the hand switch 116 or other sensor. It is also contemplated that a safety override be provided, wherein after a preset time period of substantially continuous deglutition stimulation, for example twenty seconds, or after a certain amount of stimulating energy has been delivered, for example as measured in joules, the system 20 automatically interrupts further stimulation. Although some embodiments include user-controlled initiation of the active feeding program, it should also be understood that the system 20 optionally automatically senses when a user is eating or desires to swallow, for example using one or more sensors of the sensor array 28. Also, in some embodiments, the user 90 provides user input, for example using a hand switch, as to what type of bolus and/or corresponding deglutition program should be run by the system 20.

As alluded to above, the active feeding program is optionally optimized for liquid or solid bolus consumption, consumption of boluses having different bolus volumes, or consumption of boluses having different bolus consistencies, for example, via provision of specialized programs. As will be described, stimulation according to such specialized programs is optionally modeled to exhibit a deglutition response characteristic of "normal" liquid or solid deglutition according to such conditions, e.g., deglutition of a liquid by a person not suffering from dysphagia.

In some embodiments, the user secretion maintenance program operates passively, or as a background program. In particular, the user secretion maintenance program is adapted to automatically, periodically stimulate deglutition of user secretions, such as saliva or mucous. There is evidence that an average adult produces between about 500 ml and about 1500 ml of saliva each day. Providing an automatic maintenance program facilitates disposing such user secretions without the user 90 substantially aspirating those secretions. Periodicity, i.e., the timing between deglutition sequences initiated according to the user secretion maintenance program, is optionally determined via observation of a particular individual, for example an average time that a human or other animal exhibits between secretion deglutition, or periodically stimulates deglutition as otherwise selected. The user secretion maintenance program can also be operated as part of a "night mode" operation setting of the system 20. For example, the user secretion maintenance program optionally starts and ends during a particular period, such as from 10 p.m. to 6 a.m., when the user 90 is in a substantially reclined position or state, or according to other criteria, for example. The user secretion maintenance program optionally operates continuously in the background until the active feeding program is initiated. As previously alluded to, the user secretion maintenance program includes stimulation patterns optimized for muscle activation associated with secretion deglutition in some embodiments.

Single Muscle Stimulation and Select Muscle Group Stimulation

With reference to FIG. 1, FIG. 5A, and FIG. 5B, while various embodiments include using a plurality of the deglutition muscles 54 to stimulate user deglutition, in some embodiments, the system 20 is adapted to stimulate one or more components of user deglutition using only a single one of the deglutition muscles 54 throughout a complete swallowing act. In particular, the electrode array 26 is placed in stimulating communication with a single one of the deglutition muscles 54. The single deglutition muscle is activated by placing one or more electrodes in contact with the single muscle, for example, although the single deglutition muscle can also be directly stimulated via one or more nerves controlling the single muscle, with one or more electrodes placed in stimulating communication with the single deglutition muscle via one or more of the nerves 52 to stimulate that single muscle.

Thus, in some embodiments a single deglutition muscle is artificially stimulated with the system 20 according to a stimulation program to cause a desired component of a complete deglutition act to occur. Although the single deglutition muscle is the only one of the deglutition muscles 54 directly targeted from stimulation via the electrode array 26 during the complete deglutition act, it is contemplated that some stimulating energy might inadvertently or otherwise indirectly delivered to other ones of the deglutition muscles 54, for example by current bleed or current being transmitted through the single deglutition muscle.

With reference to FIG. 5B in particular, and as alluded to above, some types of dysphagia aspiration arise as a result of an inability to activate lifting of the hyolaryngeal complex 64 to a sufficient degree and/or with appropriate timing, as well as an inability to sufficiently relax the UES 76 (FIG. 5A). Indeed, there is evidence that a substantial portion of dysphagia-related aspiration arises as a result of such defects in deglutition. In some embodiments, the hyolaryngeal complex 64 is sufficiently lifted by directly stimulating a single one of the hyoglossus 54*e*, the posterior belly of the digastric 54*d*, or the stylohyoid 54f, each of those muscles being generally represented in FIG. 5B according to a direction of movement the respective deglutition muscle 54 exerts hyolaryngeal complex 64. Thus, with reference to FIG. 5B and the foregoing, associated description, the method of stimulating a single muscle is particularly advantageous in some embodiments where the user 90 is characterized as being capable of autonomously stretching the UES 76 a sufficient amount in combination with the lifting and/or forward motion of the hyolaryngeal complex 64 provided by single deglutition muscle stimulation using the system 20 (FIG. 1). In some embodiments, a presence of sufficient, autonomous UES stretching, movement, and/or opening force is determined using the sensor array 28 (FIG. 1), as subsequently described.

With reference to FIGS. 5A and 5B, in some other embodiments, the system 20 (FIG. 1) is adapted to stimulate one or more components of user deglutition using a plurality of the deglutition muscles 54, such as one or more of those specifically described. The system 20 can operate to engender synergistic muscle movement or otherwise produce synergistic laryngeal elevation and opening of the upper esophageal sphincter using the plurality of deglutition muscles 54. The PCT App. Pub. WO 2004/028433 to inventors Ludlow et al. and entitled "Methods and Devices for Intramuscular Stimulation of Upper Airway and Swallowing Muscle Groups" (published Apr. 8, 2004) describes some systems and methods for producing synergistic laryngeal elevation and opening of the UES, the contents of which are incorporated herein by reference.

In some embodiments, the system 20 is further adapted to stimulate a targeted group of the deglutition muscles 54 including the mylohyoid, the geniohyoid, and the thyrohyoid in addition to at least one of the anterior belly of the digastric and the hyoglossus of the user 90. By stimulating the mylohyoid, the geniohyoid, and the thyrohyoid in addition to one or both of the anterior belly of digastric and the hyoglossus, it is believed the system 20 can artificially induce completed deglutition with the targeted group without any other artificial intervention.

Muscle Activation Patterns and Stimulation Patterns

Figure 7:
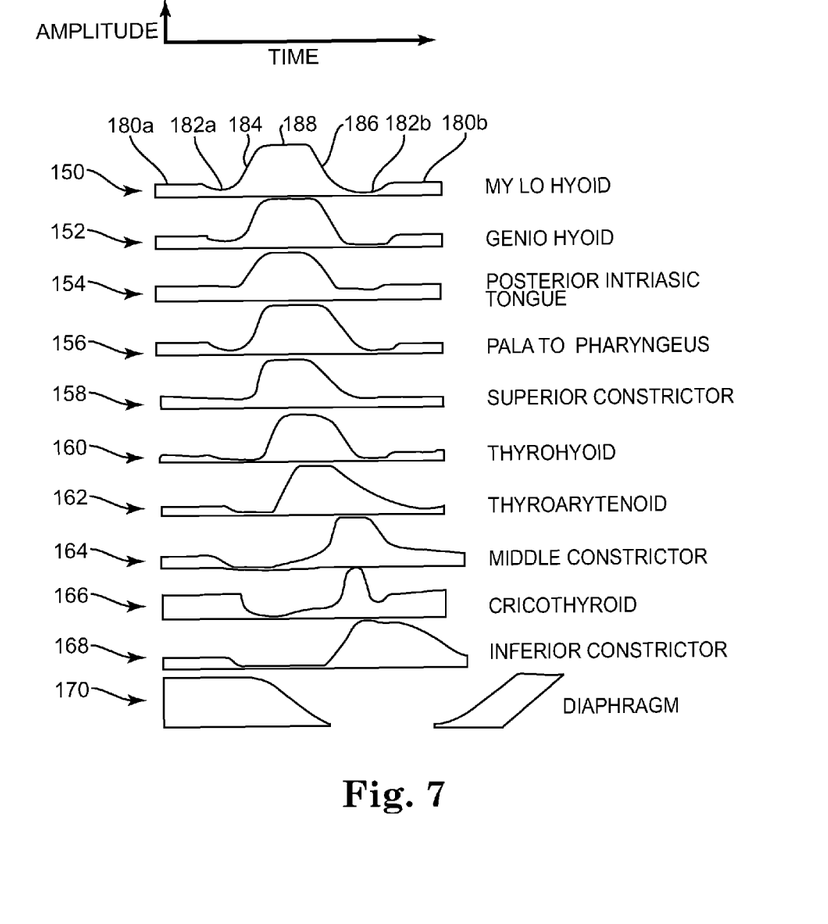
FIG. 7 illustrates several muscle activation patterns according to some embodiments.

With reference to FIG. 7 several muscle activation patterns are shown. In particular, according to some EMG studies of muscle activation during deglutition, natural muscle activation occurs over a series of sequential, overlapping patterns. FIG. 7 is illustrative of EMG measurements of muscle activation patterns in areas of a mouth, pharynx, and larynx in each of monkey, cat, and dog during deglutition as described in R. W. Doty & J. F. Bosma, *An electromyographic analysis of reflex deglutition,* 19 J. NEUROPHYSIOLOGY 44-60 (1956), the contents of which are incorporated herein by reference.

A "leading complex" of muscle activation patterns includes mylohyoid activation pattern 150, geniohyoid activation pattern 152, posterior intrinsic tongue muscles activation pattern 154, palatopharyngeus activation pattern 156, and superior constrictor activation pattern 158. Also included are activation patterns of the palatoglossus, styloglossus, and stylohyoid (not shown) as part of the "leading complex." The leading complex activation patterns initiate deglutition, showing concurrent elevated muscle activity for between about 250 milliseconds and about 500 milliseconds.

Other delayed muscle activation patterns show inhibited onset of elevated muscle activity, including thyrohyoid muscle activation pattern 160, thyroarytenoid activation pattern 162, middle constrictor activation pattern 164, cricothyroid activation pattern 166, inferior constrictor activation pattern 168, and diaphragm activation pattern 170. In fact, the inferior constrictor activation pattern 168 shows deferred muscle activation until elevated muscle activity of the leading complex is nearly over. Several of the leading complex and delayed activation patterns exhibit features such as baseline activation, decreased transient activation, increasing activation ramping, and/or decreasing activation ramping. For example, the mylohyoid activation pattern 150 shows baseline activation segments 180a, 180b, decreased transient activation segments 182a, 182b, an increasing ramp segment 184, a decreasing activation ramp 186, and an elevated activation segment 188.

In some embodiments a stimulation program or programs are determined or set according to activation patterns, such as those described above, including activation of a leading muscle complex and delayed activation patterns for other deglutition muscles as desired. In order to obtain one or more activation patterns for the deglutition muscle(s) 54, averaged natural deglutition muscle stimulation patterns are optionally determined from a test group such as a group of healthy, dysphagia-free test subjects. The stimulation program then sets or drives deglutition muscle stimulation to imitate the averaged natural deglutition muscle activation patterns. In some embodiments, individual natural deglutition muscle stimulation patterns for a particular individual are measured or calculated to determine a customized activation pattern. In some embodiments, the stimulation program then sets or drives deglutition muscle stimulation to the customized pattern. In other embodiments, theoretical natural deglutition muscle stimulation patterns are derived from empirical data, qualitative observation, user feedback, measurement of actual bolus deglutition with various applied stimulation patterns, and/or via other means. Such theoretical and/or iterative evaluation techniques may be particularly advantageous where the user 90 is a sufferer of dysphagia and appropriate natural deglutition stimulation patterns are not directly measurable from the user 90.

Furthermore, particular categories of deglutition are optionally measured or modeled, for example liquid deglutition, solid deglutition, and/or user secretion deglutition. In at least this manner, specialized feeding programs, such as a specialized liquid or solid deglutition programs, user secretion maintenance programs, or even changes in deglutition according to body position or environment, for example when the user 90 is in a reclined position, is at high altitude, is under water, and others, are optionally identified by measuring or modeling deglutition muscle activation when the user 90 or test group is swallowing such boluses and/or is in the states described.

With reference between FIGS. 1 and 7, in some embodiments, the system 20 uses one or more of the stimulation programs to stimulate a plurality of the deglutition muscles 54 to imitate natural deglutition muscle activation patterns. For example, some embodiments include using the signal generator 24 to cause the electrode array 26 to stimulate the deglutition muscles 54 with a group of sequential and overlapping electrical pulse trains in order to activate the deglutition muscles 54 similarly to sequential, overlapping patterns of muscle activation, such as those illustrated in FIG. 7. In some embodiments, the group of sequential and overlapping electrical pulse trains includes at least one asymmetric, biphasic waveform.

Thus, in some embodiments, the stimulating electrical pulse trains themselves imitate the muscle activation patterns, or have somewhat similar amplitude and timing to the muscle activation patterns. In other embodiments, regardless of whether electrical pulses delivered by the system 20 are delivered to the deglutition muscles 54 (FIG. 5A) as sequential and overlapping pulses, the stimulating energy pattern delivered by the electrode array 26 is configured such that resultant activation patterns of the plurality of deglutition muscles 54 imitate or are similar to a desired set of activation patterns. Furthermore, analogously to the muscle activation patterns described above, the system 20 optionally delivers one or more electrical pulses defining one or more stimulation pattern features, such as baseline segments, decreased transient segments, increasing ramps, decreasing ramps and/or others, such features imitating corresponding muscle activation pattern features, or others.

In some embodiments, baseline segments are included in the stimulation patterns or baseline activation segments are otherwise simulated to adjust muscle tension before triggering a component of deglutition associated with a particular deglutition muscle 54. In some embodiments, baseline segments in a stimulation program optionally serve to place deglutition musculature of the user 90 in a state of partial activation prior to at least one of activation of the partially activated deglutition musculature via autonomous user stimulation and artificial activation of the partially activated musculature via the system 20. As evidenced by FIG. 7, many of the deglutition muscles 54 exhibit baseline activity prior to full muscle activation. Incorporating a baseline stimulation segment in the stimulation program pattern for a deglutition muscle can serve various roles, including, for example, adjusting muscle slack and hyolaryngeal position in preparation for deglutition and/or providing proprioceptive and tactile user feedback to a central nervous system of the user 90.

FIG. 7 also evidences that many of the deglutition muscles 54 (FIG. 5A) exhibit decreased transient activity before and/or after full muscle activation. In some embodiments, decreased transient segments are also present in stimulation program patterns or decreased transient activation is otherwise simulated. In some embodiments, decreased transient activation serves to inhibit baseline activation activity as described above, with such inhibition occurring just prior to and/or following full activation of one or more of the deglutition muscles 54.

User Feedback and Deglutition Timing with Artificial Deglutition Stimulation

With reference to FIGS. 1 and 5, in some embodiments, user feedback helps the user 90 time autonomous deglutition efforts with the artificial stimulation provided by the system 20. In particular, some embodiments include the user 90 autonomously providing some of the movement required for deglutition in response to the user feedback, with the system 20 also providing stimulation for remaining deglutition movement to help prevent aspiration as desired. For example, the user 90 is optionally provided with a subthreshold, baseline signal prior to user deglutition, such as the baseline signals described above, which provides proprioceptive user feedback. In turn, artificial stimulation of deglutition musculature with the system 20 is coordinated with the user feedback, for example at a desired timing or delay between initiation of the baseline signal and initiation of a stimulating signal by the system 20. Additionally, or alternatively, the user feedback optionally can also serve to help "retrain" the user 90 how to swallow, such that the user feedback is part of a therapeutic program.

In some embodiments user feedback is additionally or alternatively provided by stimulating sensory mucosa (not shown) of at least one of the mouth and throat of the user 90, such as sensory mucosa associated with the hyolaryngeal complex 64 and/or pharynx P to provide tactile, sensory feedback to the user 90. In particular, one or more electrodes of the electrode array 26 are placed in stimulating communication with sensory mucosa of the hyolaryngeal complex 64 or the pharynx P, for example. During artificial deglutition stimulation, the system 20 stimulates the sensory mucosa to provide tactile user feedback as desired. It should be understood that it is contemplated that any sensory mucosa of the deglutition components 50 could be stimulated to provide user feedback. Also, as described above, other embodiments alternatively or additionally include using subthreshold, baseline or other low-level muscle stimulation signal with the electrode array 26 to provide proprioceptive feedback. In some embodiments, sensory feedback is provided by placing one or more electrodes in direct stimulating communication with one or more of the nerves 52.

Artificial Deglutition Muscle Stimulation Via Nerves

As referenced above, while the system 20 is optionally adapted to deliver stimulating energy to one or more of the deglutition muscles 54 by placing contacts of the electrode array 26 in or on deglutition musculature, some embodiments also include stimulating one or more deglutition muscles 54 via the nerves 52 as will be described with reference between FIG. 1, FIG. 5A, and FIG. 8. For example, the various stimulation programs and/or muscle activation patterns described above are optionally delivered via stimulation of deglutition musculature by stimulating the nerves 52 with the electrode array 26 or by stimulating the deglutition muscles 54 using electrodes implanted on (epimysial electrodes) or in (intramuscular electrodes) the deglutition muscles 54, for example. With that in mind, some embodiments including artificial deglutition muscle stimulation via the nerves 52 are described in greater below.

With particular reference to FIG. 8, a schematic illustration of the electrode array 26 placed in stimulating communication with the first and second nerves 52a, 52b is shown. For reference, FIG. 8 illustrates various deglutition components 50 previously described, and also presents a schematic view of a tooth 200 and a tongue 210 of the user 90. In some embodiments the first electrode 26a of the electrode array 26 is adapted for stimulating nerves, for example being substantially similar to embodiments of the nerve cuff electrode 40 (FIG. 3) previously described. The second electrode 26b is similarly configured, also optionally being a nerve cuff electrode substantially similar to embodiments of the nerve cuff electrode 40. For reference, one or both of the first and second nerves 52a, 52b optionally provide sensory and/or motor functionality, with deglutition muscle response occurring as a result of sensory stimulation or motor function stimulation.

With additional reference to FIGS. 1 and 5, in some embodiments, the system 20 is adapted for selectively stimulating nerve fascicles of the nerves 52 in order to activate one or more of the deglutition muscles 54 to assist with any one or more of the stages of deglutition. For a discussion of selective muscle stimulation and acceptable electrode types see, for example, M. D. Tarler & J. T. Mortimer, *Elective and independent activation of four motor fascicles using a four contact nerve-cuff electrode,* 12(2) IEEE TRANSACTIONS ON NEURAL SYS. REHAB. ENG'G 251-257 (2004); W. M. Grill & J. T. Mortimer, *Inversion of the current-distance relationship by transient depolarization,* IEEE TRANSACTIONS ON BIOMEDICAL ENG'G 1-9 (1997); U.S. Pat. No. 5,344,438, issued Sep. 6, 1994 to inventors Testerman et al. and entitled "Cuff Electrode;" and U.S. Pat. No. 6,907,293, issued Jun. 14, 2005 to inventors Grill et al. and entitled, "Systems and Methods for Selectively Stimulating Components in, on, or near the Pudendal Nerve or Its Branches to Achieve Selective Physiologic Responses"), the contents of each of which are incorporated herein by reference. In general terms, selective stimulation can be advantageous where non-selective stimulation of one or more of the nerves 52 would result in improper timing or interfere with other stages of swallowing. For example, stimulation of the hypoglossal nerve without selective fascicle stimulation could result in early activation of the styloglossus and the intrinsic muscles of the tongue, which would otherwise interfere with the oral stage of swallowing.

Regardless, in some embodiments, each of the first and second electrodes 26a, 26b is adapted to allow selective stimulation of nerves and is placed in stimulating communication with one of the nerves 52, and thus one or more of the deglutition muscles 54. In some embodiments, the first electrode 26a is disposed about the first nerve 52a, which is the hypoglossal nerve, for example. In turn, the second electrode 26b is disposed about the second nerve 52b, which is the mylohyoid nerve, for example. In particular, the first electrode 26a is located on the first nerve 52a to deliver stimulating energy to the nerve fascicles 60 of first nerve 52a for stimulating or otherwise causing activation of one or more of the geniohyoid, hyoglossus, thyrohyoid, omohyoid, sternothyroid, sternohyoid, genioglossus, and styloglossus muscles. In turn, the second electrode 26b is located on the second nerve 52b to deliver stimulating energy to the nerve fascicles 62 of the second nerve 52b for stimulating or otherwise causing activation of one or more of the mylohyoid and a digastric muscle, for example. In particular, some embodiments include selectively stimulating activation of one or more of the hyoglossus, geniohyoid, and thyrohyoid muscles by selectively stimulating fascicles of the first nerve 52a and selectively stimulating activation of one or more of the mylohyoid and anterior belly of the digastric muscles by selectively stimulating fascicles of the second nerve 52b.

In some embodiments where bilateral stimulation desired, the third and fourth electrodes 26c, 26d are placed on an opposite side of the user 90 in communication with second hypoglossal and mylohyoid nerves opposite the first and second nerves 52a, 52b, for example. The third and fourth electrodes 26c, 26d are optionally substantially similar in form and operation to the first and second electrodes 26a, 26b, and thus are left from further discussion.

Regardless, where selective stimulation is appropriate, the controller 22 is adapted to operate the signal generator 24 to selectively stimulate one or more fascicles of the nerves 52 with the electrode array 26, such as the fascicles 60 of the first nerve 52a and/or the fascicles 62 of the second nerve 52b. Some embodiments include selectively stimulating the first fascicle 60a of the first nerve 52a, selectively stimulating the second fascicle 60b of the first nerve 52a, and selectively stimulating the third fascicle 60c of the first nerve 52a, where each of the first, second, and third fascicles 60a-60c control activation of a different deglutition muscle than the others. Similarly, embodiments include selectively stimulating the first fascicle 62a of the second nerve 52b and selectively stimulating the second fascicle 62b of the second nerve 52b, the first fascicle 62a controlling activation of a different deglutition muscle than the second fascicle 62b, and so forth.

In order to accomplish selective fascicle stimulation, some embodiments include using the signal generator 24 to deliver subthreshold, rectangular current pulses, or current ramps to partially depolarize nerve fibers of the first and/or second nerves 52a, 52b using the first and/or second electrodes 26a, 26b. As used herein, the term "subthreshold" is indicative of an insufficient amount of stimulation to result in full muscle activation. Additionally, for reference, and in brief, stimulation of the nerves 52 is generally characterized by a strength-to-distance relationship, where fascicles closer to a source of stimulating energy, for example an electrical current pulse delivered from the electrode array 26, are stimulated first and/or to a greater extent. By using subthreshold, rectangular current pulses or ramps, the strength-to-distance relationship is optionally inverted, such that fascicles can be selectively stimulated by partially depolarizing a corresponding nerve. In other words, the system 20 can be configured to selectively stimulate a fascicle or group of fascicles more distant from the stimulating electrode than a closer group of fascicles, and prior to the closer group of fascicles, by depolarizing the nerve.

Additionally or alternatively, the strength-to-distance relationship described above is taken advantage of in some embodiments by placing electrode contacts at various positions on or around one or more of the nerves 52. By delivering a standard current pulse, for example a 100-μs rectangular current pulse, to a particular location on the one or more nerves 52, nerve fascicles closest to a particular contact are stimulated first or to a sufficient degree to result in muscle activation of one or more of the deglutition muscles 54. Thus, selectivity is also optionally accomplished by placing contacts at various locations about a nerve more proximate a fascicle group that is to be stimulated.

As yet another, non-exclusive means for accomplishing selective fascicle stimulation, current steering techniques are optionally employed. In some embodiments, the first and second electrodes 26a, 26b are substantially similar to embodiments of the nerve cuff electrode 40 (FIG. 3) previously described, with each of the first and second electrodes 26a, 26b including a plurality of radially positioned monopolar contacts, for example four monopolar contacts per electrode, although bipolar contacts are contemplated in some embodiments. The signal generator 24 is configured to operate over multiple channels to deliver varying amounts of stimulating energy to each of the radially positioned contacts. In particular, subthreshold steering currents are applied about the nerve, for example the first nerve 52a, at different amplitudes in order to shape an electrical field applied to the nerve as desired. The subthreshold steering currents do not necessarily result in nerve stimulation. In particular, in some embodiments, the steering currents are applied about one of the nerves 52, for example the first nerve 52a, to direct another, stimulus pulse or series of pulses generated with the first electrode 26a or another electrode to a desired region of nerve activation. In other words, the steering currents are used to direct an additional stimulating current pulse or pulses to a selected fascicle or group of fascicles.

Additionally, stimulation pattern waveforms are optionally selected to improve an ability to selectively stimulate nerve fascicles of the nerves 52. For example, short duration current pulses have been identified as increasing stimulation threshold differences between nerve fibers of different diameters. While several mechanisms for accomplishing selective fascicle excitation/stimulation have been described above, it should be understood that other mechanisms are also contemplated, including electrical blocking of nerves/nerve fascicles.

In some other embodiments, the first and second electrodes 26a, 26b are located along the nerves 52 at a location where selective stimulation of nerve fascicles in order to activate desired deglutition musculature is not required.

In particular, the first and second electrodes 26a, 26b are optionally located along a nerve branch rather than a nerve trunk, for example a peripheral branch of the hypoglossal nerve, sufficiently proximate one or more of the deglutition muscles 54, such that a desired timing of activation of a desired set of the deglutition muscles 54 is accomplished without selectively stimulating nerve fascicles. Thus, the electrode array 26 additionally or alternatively includes a plurality of electrodes disposed along, and in stimulating communication with, a plurality of nerves in order to effectuate deglutition musculature stimulation without selective fascicle stimulation.

System Feedback

With reference to FIGS. 1 and 6 and turning back to the sensor array 28, in some embodiments, the sensor array 28 provides the system 20 means for operating with system feedback. For example, the stimulation programs described above are optionally initiated, modified, or otherwise adapted according to sensor input information received by the controller 22. Various sensors and their use are described below. For example, in some embodiments, the sensor array 28 includes sensors configured and placed, for example subcutaneously and/or intramuscularly, to provide EMG feedback to the system 20. Such EMG feedback is optionally used to drive a stimulation program to a predetermined, optimal muscle activation pattern as measured via the EMG feedback.

In some embodiments, the sensor array 28 includes one or more force sensors, such as strain gauges, providing force information to the controller 22. According to some applications, one or more of the strain gauges are attached to one or more deglutition muscles 54 to provide force information during various states of muscle activation. For example, in some embodiments, the first sensor 28a is a strain gauge and is attached to the UES 76 to provide information relating to an opening force applied to the UES 76. Such force information is optionally used by the system 20, and in particular the controller 22, to optimize a stimulation program or otherwise provide system feedback information for modifying deglutition muscle stimulation.

In still other embodiments, the sensor array 28 includes one or more positional sensors, such as accelerometers providing such information as acceleration, velocity, or position. In some embodiments the first sensor 28a is a three-axis accelerometer providing head position information and is optionally secured relative to the chin, for example the mental protuberance 110. With additional reference to FIG. 5A, the second sensor 28b, in turn, is a three-axis accelerometer secured relative to one or more deglutition components 50, such as a portion of the hyolaryngeal complex 64 of the user 90. For example, the second sensor 28b is optionally secured relative to the hyoid 70 or other laryngeal cartilage, such as the thyroid cartilage. In some embodiments, the second sensor 28b is optionally oriented parallel to the anterior-posterior and rostro-caudal axes $H_{AP}$, $H_{AR}$ of the laryngeal complex 64 or components thereof. Still yet, the third sensor 28c is optionally a three-axis accelerometer secured relative to the implantable housing 32.

In some embodiments, overall body position information of the user 90 is provided by the sensor array 28, and in particular the third sensor 28c. Movement of the hyolaryngeal complex 64 or components thereof relative to a torso of the user 90 is provided using combined positional information from the second and third sensors 28b, 28c. This information relating to relative positions of the torso and hyolaryngeal complex 64 can then be used to optimize deglutition stimulation with the system 20 for a desired relative movement of the deglutition structures 54, such as the hyolaryngeal complex 64 or portions thereof. In turn, neck flexion information is optionally provided using combined positional information from the sensor 28a secured relative to the chin and the second sensor 28b secured relative to the laryngeal complex 64 or portions thereof. In this manner, the system 20 compensates for neck flexion during deglutition stimulation. Additionally or alternatively, in some embodiments, the sensor array 28 provides information related to whether the user 90 is in a reclined state, for example in order to determine whether to select the user secretion maintenance program or to optimize swallowing for a reclined position.

Although combined utilization of positional information is contemplated as referenced above, non-combined positional information from a single position sensor, such as a three-axis accelerometer is also optionally used to optimize or otherwise modify deglutition stimulation with the system 20. In some embodiments, information relating to whether the hyolaryngeal complex 64 is being adequately lifted and moved forward is obtained where a standard orientation of the body of the user 90 is assumed and an accelerometer, for example one of the three-axis accelerometers as previously referenced, is oriented parallel to the anterior-posterior and rostro-caudal axes $H_{AP}$, $H_{AR}$ of the hyolaryngeal complex 64 or components thereof, for example.

In still other embodiments, the sensor array 28 includes one or more pressure sensors, for example sensors for measuring intrapharyngeal pressure. For example, intrapharyngeal pressure is optionally measured as an indicator of effective deglutition stimulation and/or artificial response.

With reference between FIG. 1, FIG. 5A, and FIG. 6, in some embodiments, the sensor array 28 alternatively or additionally includes one or more displacement sensors providing displacement information, such as sonomicrometers (not shown) including ultrasonic sensing and generating crystals to measure distance between crystals. One or more of the first, second, and third sensors 28a-28c are optionally sonomicrometers attached to one or more components of the hyolaryngeal complex 64. In some embodiments, the sensors 28a-28c are used to provide displacement information relating to lengths of one or more of the deglutition muscles 54. In particular, displacement of various deglutition structures 56 can be derived, or otherwise estimated, using such overall muscle length information. Additionally or alternatively, such displacement sensors are used in a substantially similar manner to the positional sensors as described above in order to optimize or otherwise modify stimulation programs. For example, relative positions of the hyolaryngeal complex 64, including the hyoid 70, the chin, and/or the thyroid cartilage, are optionally provided by the sensor array 28 to adjust deglutition stimulation. In some embodiments, a thyroid-hyoid gap is determined using the displacement sensors with stimulation of the thyrohyoid muscle applied proportionally to the thyroid-hyoid gap.

In sum, and in accordance with the understanding provided by the textual descriptions, figures, and the accompanying claims, systems for assisting deglutition and methods for constructing and using systems for assisting deglutition have been disclosed, taught, and suggested, with such systems and methods serving a variety of purposes, such as helping provide deglutition with reduced aspiration. Such systems and methods of assisting deglutition have applicability for use with at least humans or other animals and are useful as either partially or entirely external or non-implanted systems, as well as entirely implanted or internal systems. Although the present invention has been described with reference to various embodiments, workers skilled in the art will recognize that changes can be made in form and detail without departing from the spirit and scope of the present invention. For example, although systems and methods associated with deglutition have been described herein, it should also be understood that principles of the present invention are applicable to other areas of muscle stimulation, for example speech, breathing, or other types of bodily movement.

What is claimed is:

1. A method of controlling deglutition of a user without substantial aspiration comprising:
   subcutaneously positioning a first electrode array at a first location along a first nerve comprising a first fascicle controlling a first deglutition muscle and a second fascicle controlling a second deglutition muscle,
   wherein the electrode array comprises at least one electrode, and further wherein the first nerve is associated with the first deglutition muscle and the second deglutition muscle such that stimulation of the first nerve causes movement of at least one of the first deglutition muscle and the second deglutition muscle; and
   selectively stimulating the first fascicle with the first electrode array to artificially activate the first deglutition muscle independent of activation of the second deglutition muscle;
   wherein the first deglutition muscle is selected from the group consisting of tongue, hyoglossus, genioglossus, constrictor pharyngis, cricopharyngeous, digastricus, cricoarytenoid laterlis, geniohyoid, levator veli palatini, mylohyoid, omohyoid, palatoglossus, palatopharyngeus, sternohyoid, sternothyroid, styoglossus, stylohoid, stylopharyngeus, and tensor veli palatine muscles;
   selectively stimulating the second fascicle with the first electrode array to artificially activate the second deglutition muscle independent of activation of the first deglutition muscle; and
   wherein only fascicles of the first nerve are artificially stimulated throughout user deglutition.

2. The method of claim 1, wherein the first nerve is a hypoglossal nerve and further wherein each of the first and second deglutition muscles are selected from the group consisting of geniohyoid and hyoglossus muscles of the user.

3. The method of claim 1, wherein the first nerve causes artificial activation of the first deglutition muscle via sensory activation of the first deglutition muscle.

4. The method of claim 1, wherein the electrode array comprises a plurality of radially positioned contacts disposed about the first nerve at the first location, and further wherein stimulating the first fascicle comprises simultaneously providing subthreshold currents through the plurality of radially positioned contacts of the electrode array for steering a stimulation signal delivered to the first fascicle.

5. The method of claim 1, wherein the first nerve comprises a first fascicle controlling the first deglutition muscle, the method further comprising:
   partially depolarizing the first nerve after stimulating the first fascicle.

6. The method of claim 5, wherein partially depolarizing the first nerve comprises stimulating the first nerve with a subthreshold rectangular pulse.

7. The method of claim 1, further comprising:
   subcutaneously positioning the electrode array in stimulating communication with a mylohyoid, a genihyoid, and a thyrohyoid and at least one of an anterior belly of a digastric and a hyoglossus of the user.

8. The method of claim 1, wherein the electrode array includes an electrode selected from the group consisting of a self-contained electrode, an intramuscular electrode, an epimysial electrode, and a nerve cuff.

9. A system for assisting user deglutition comprising:
   an electrode array adapted to be subcutaneously implanted to stimulate a first nerve comprising a first fascicle and a second fascicle, the first fascicle causing activation of a first deglutition muscle and the second fascicle causing activation of a second deglutition muscle, the electrode array including a plurality of electrode contacts;
   a signal generator adapted to communicate with the electrode array to stimulate the first nerve; and
   a controller for operating the signal generator, wherein the controller is programmed to operate the signal generator to selectively stimulate the first fascicle with the electrode array to cause activation of the first deglutition muscle independent of activation of the second deglutition muscle and selectively stimulate the second fascicle with the electrode array to cause activation of the second deglutition muscle independent of activation of the first deglutition muscle, including the controller programmed to simultaneously deliver varying amounts of energy to each of the plurality of electrode contacts as subthreshold steering currents configured to direct an additional stimulating current pulse to a selected region of the first nerve.

10. The system of claim 9, wherein the signal generator and the electrode array are housed together as a single unit adapted to be subcutaneously implanted.

* * * * *